United States Patent [19]

Brace

[11] 4,144,244

[45] Mar. 13, 1979

[54] PERFLUOROALKYL-IODO NORBORNANE DICARBOXYLIC ACIDS AND DERIVATIVES THEREOF

[75] Inventor: Neal O. Brace, Wheaton, Ill.

[73] Assignee: Ciba-Geigy Corporation, Ardsley, N.J.

[21] Appl. No.: 865,060

[22] Filed: Dec. 27, 1977

[51] Int. Cl.² .................. C07D 209/76; C07D 307/93; C07C 61/12

[52] U.S. Cl. .......................... 260/326 C; 260/343.3 R; 260/346.3; 562/502; 260/544 L; 260/544 F; 260/557 B; 560/117; 560/120

[58] Field of Search ............ 260/326 C, 346.3, 514 G, 260/544 L, 544 F, 557 B; 560/120

[56] References Cited

U.S. PATENT DOCUMENTS

| | | | |
|---|---|---|---|
| 2,314,846 | 3/1943 | McClellan et al. | 560/120 |
| 3,145,222 | 8/1964 | Brace | 260/408 |
| 3,784,509 | 1/1974 | Dotson et al. | 260/326 HL X |
| 3,989,725 | 11/1976 | Brace | 260/346.3 |
| 4,082,798 | 4/1978 | Brace | 260/557 B |

OTHER PUBLICATIONS

Smart, J. Org. Chem., vol. 38 (1973) pp. 2027, 2035 & 2039.

Osborn et al., J. Am. Chem. Soc., vol. 90 (1968) p. 5806.
Ludwick et al., J. Org. Chem., vol. 34 (1969) p. 4108.
Brace, J. Org. Chem., vol. 27 (1962) p. 3027.

*Primary Examiner*—Richard Raymond
*Attorney, Agent, or Firm*—Edward McC. Roberts; Michael W. Glynn

[57] ABSTRACT

The compounds disclosed are of the formula

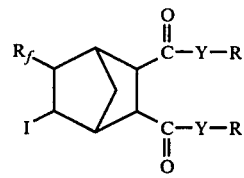

and the anhydrides thereof wherein
$R_f$ is a perfluoroalkyl group,
Y is oxygen, or an amine, and
R is hydrogen or alkyl.

These compounds can be prepared by a free radical catalyzed addition of a perfluoroalkyl iodide to a 5-norbornene diacid or its derivative. They are useful in preparing surfactants when reacted with an amine.

13 Claims, No Drawings

PERFLUOROALKYL-IODO NORBORNANE DICARBOXYLIC ACIDS AND DERIVATIVES THEREOF

DETAILED DISCLOSURE

The compounds of this invention are perfluoroalkyliodo norbornane derivatives of the formulae

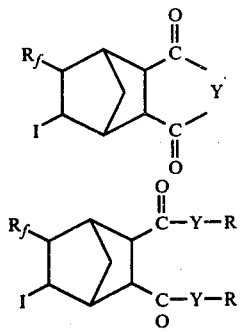

I and II wherein

Y is independently oxygen or the group $>$ NR

R is independently hydrogen or alkyl of 1 to 24 carbons or each group — YR is independently a halogen and $R_f$ is a straight or branched chain perfluoroalkyl of 1 to 18 carbon atoms or said perfluoroalkyl substituted by a perfluoroalkoxy group of 2 to 6 carbon atoms.

The anhydride or diacid compounds of this invention possess low free surface energies and provide solutions of low surface and interfacial tension in water and hydrocarbon solvents which makes them useful as surfactants. They are also useful in the preparation of perfluoroalkyl and iodo group containing polyesters or polyamides. In preparing these polymers the above compounds are employed as the known anhydrides and diacids. The anhydrides or diacid compounds, when converted to simple metal salts show pronounced surface activity in aqueous media. Therefore they are useful as wetting or dispersion agents.

The exact nature of the group $R_f$ is not of critical importance as far as the compounds of this invention are concerned. For the sake of illustration, however, this group can be represented by such formulae as $-C_pF_{2p+1}$ and $-C_qF_{2q}OC_pF_{2p+1}$ where $p$ is 1 to 18 and preferably 6 to 12 and $q$ is 2 to 8.

The R groups are independently hydrogen or alkyl of 1 to 24 carbons and preferably of 1 to 6 carbons. Thus where Y is oxygen and both R groups are hydrogen the resulting compound is a dicarboxylic acid. If one R group is hydrogen and the other is alkyl, the resulting compound is a half ester, and when both R groups are alkyl, the compound is a diester. If Y is sulfur then the corresponding thioacids or thioesters results. When Y is an $>$NR group then an amido or an alkyl substituted amido compound results, depending on the definition of R.

Where X is oxygen the resulting compound is an anhydride and when it is $>$NR an imide is obtained. The compounds of formula II encompass acid halides when —YR is a halogen selected from chlorine, bromine or fluorine. Either both —YR groups can be acid halides or one —YR can be an ester, acid or amide while the other is an acid halide.

The above represented compounds can be obtained by a free radical catalyzed addition of a polyfluoroalkyliodide of the formula $R_fI$ to a 5-norbornene diacid, anhydride or a derivative thereof having a formula

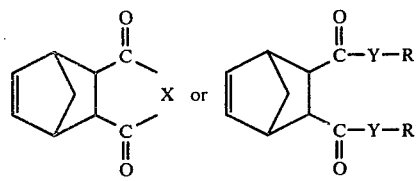

The norbornene reactant may have endo or exo cis configuration or it may have trans configuration when one —YR group is endo and the other exo. Therefore the compounds may exist in an isomeric mixture. The configuration of the norbornene reactant is normally retained in the addition product.

The various norbornene derivatives are available commercially. They can also be prepared by the methods described below.

The Diels-Alder addition of maleic anhydride to cyclopentadiene gives only the endo adduct, 5-norbornene-endo,endo-2,3-dicarboxylic anhydride. When dimethyl maleate is employed as the dienophile, the analogous reaction gives dimethyl 5-norbornene-endo,endo-2,3-dicarboxylate. Since the reaction is stereospecific, dimethyl fumarate or fumaric acid provides the corresponding trans-adducts. These unsaturated substances are the starting materials for the new products of this invention. Alternative routes to many of these starting materials are also known. For example, the esters may be made from the 5-norbornene-2,3-dicarboxylic anhydrides, or the trans-adducts may be obtained from the cis-adducts, by isomerization. There is only one known way to obtain the exo-anhydride, which is by isomerization of the endo-anhydride, but from 5-norbornene-exo,exo-2,3-dicarboxylic acid anhydride the whole series of related derivatives may then be prepared.

The free radical initiators that can be employed in the reaction are azo-nitriles and azo-derivatives which dissociate into alkyl- or aryl-radicals at reaction temperatures. The best known example of an azo-nitrile is 2,2'-azobisisobutyronitrile and the dissociation providing the required alkyl-radical is shown as follows:

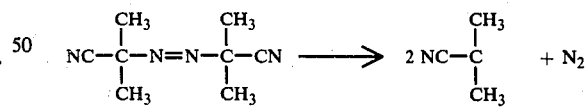

Other azo-nitriles are azo-derivatives which can be used are described in J. Brandrup and E. H. Immergut, Polymer Handbook (John Wiley & Sons) 1965 pages II-3 to II-14 and include, for example 2-cyano-2-propyl-aza-formamide
2,2'-azo-bis-isobytyronitrile
2,2'-azo-bis-2-methylpropionitrile
1,1'-azo-bis-1-cyclobutanenitrile
2,2'-azo-bis-2-methylbutyronitrile
4,4'-azo-bis-4-cyanopentanoic acid
1,1'-azo-bis-1-cyclopentanenitrile
2,2'-azo-bis-2-methylvaleronitrile
2,2'-azo-bis-2-cyclobutylpropionitrile
1,1'-azo-bis-1-cyclohexane nitrile
2,2'-azo-bis-2,4-dimethylvaleronitrile 2,2'-azo-bis-2,4,4-trimethylvaleronitrile
2,2'-azo-bis-2-benzylpropionitrile
1,1'-azo-bis-1-cyclodecane nitrile
azo-bis-(1-carbomethoxy-3-methylpropane)
phenyl-azo-diphenylmethane
phenyl-azo-triphenylmethane
azo-bis-diphenylmethane
3-tolyl-azo-triphenylmethane Certain peroxide-initiators can also be useful in preparing the compounds of the present invention. These peroxide-initiators all decompose instantly into alkyl- or aryl-radicals. The alkyl- or aryl-radical is obtained either by instantaneous decomposition or by a rearrangement reaction of the primary decomposition products of the peroxide compound. Of the peroxides, the aryl peroxides are, for example, most useful and one preferred aryl peroxide is benzoyl peroxide. The decomposition of this compound into alkyl-radicals can be set out as follows:

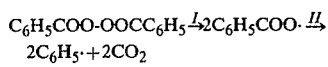

$2C_6H_5\cdot + 2CO_2$

Reaction II follows Reaction I instantaneously. In the presence of iodine, only $C_6H_5I$ is isolated; proof of the instantaneous formation of the phenyl radical. In addition to benzoyl peroxide, lauroyl peroxide and alkanoyl peroxides containing up to 18 carbon atoms are also useful as initiators. Such peroxide compounds include propionyl peroxide, butyryl peroxide, isobutyryl peroxide, cyclobutaneacetyl peroxide, heptanoyl peroxide, caprylyl peroxide, cyclohexane acetyl peroxide, nonanoyl peroxide, myristoyl peroxide, stearyl peroxide, ditertiary butyl peroxide, acetyl peroxide and the like.

The free radical initiator is employed in the amounts of from 0.01 to 0.5 moles per mole of the norbornene starting compound and more preferably from 0.02 to 0.1 moles. The reaction is carried out at a temperature of from about 40° C. to about 150° C. either in bulk or in an inert solvent which does not interfere with the reaction. Illustrative examples of appropriate solvents are hydrocarbon solvents such as benzene, toluene, cresol, xylene, cyclohexane, pentane, hexane. Other solvents that may be also employed are ethyl acetate, dioxane, acetone, dimethylformamide, dimethylsulfoxide, pyridine, dimethylsulfone, tetrahydrofuran, chloroform, nitrobenzene, cyclohexanone.

The addition reaction can be also carried out without the initiator, but then the reaction must be carried out at a higher temperature, such as 150° C. to 200° C. It is also possible to utilize ultraviolet radiation either alone or in combination with a free radical initiator. To accomplish the reaction under these conditions the reaction temperature may range from 10° C. to about 150° C.

Preferably the reaction is carried out in bulk, without a solvent medium, and in the presence of a free radical initiator, especially 2,2'-azo-bis-isobutyronitrile.

As noted above, 5-norbornene-2,3-endo, endo-dicarboxylic acid anhydride is available commercially. The corresponding esters can be prepared according to known methods, for example the dimethyl and the diethyl esters can be prepared by the method described by Morgan et al, J. Am. Chem. Soc. 66, 404 (1944) and Bauer et al, J. Org. Chem., 26, 1106 (1961).

The half alkyl esters can be prepared by the method of L. M. Rice and E. E. Reid, J. Am. Chem. Soc., 74, 3955 (1952), or H. M. Walton, J. Org. Chem., 22, 308 (1957). 5-Norbornene-2,3-exo, endo-dicarboxylic acid can be prepared by the method of H. Koch, J. Kotlan and H. Markut, Monatsh., 96, 1646 (1965) or of J. Sauer. H. Wiest and A. Mielert, Chem. Ber., 97, 3183 (1964). N-phenyl, N-tolyl and N-benzylimides of 5-norbornene-2,3-endo, endo (or exo, exo)-dicarboxylic acids can be prepared by the method of M. S. Morgan, R. S. Tipson, A. Lowry and W. E. Baldwin, J. Am. Chem. Soc., 66, 404 (1944). Many of these 5-norbornene-2,3-dicarboxylic acid derivatives can be prepared by the Diels-Alder reaction, as described by M. C. Kloetzel, Org. Reactions, Vol. IV, 1, (1948).

The two alternative routes to endo-5-iodo-exo-6-perfluoroalkylnorbornane-endo, endo-2,3-dicarboxylic acids are shown below:

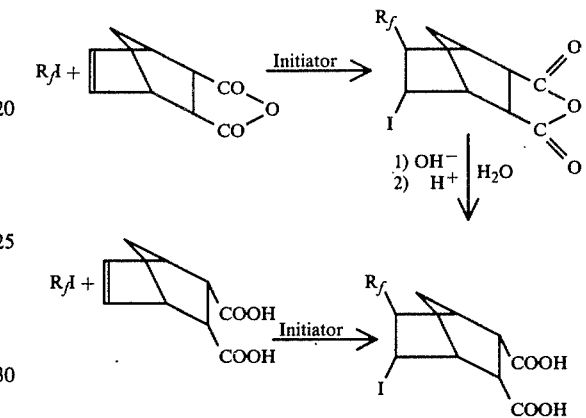

In a similar fashion the acids, esters, amides or alcohols of this invention can be prepared from the corresponding norbornene derivative in the manner most suitable to the purpose. The anhydride is particularly useful as it is readily converted to a large number of new compounds in high yield. There may be instances where the properties of the desired final product are such that it is more practical to follow one or the other procedure. Also, the precursor of the final product may be very difficult or impossible to prepare by a given route, but may be obtained by an alternate route. For example, the sodium salts of 5-norbornene-endo,endo,endo-2,3-dicarboxylic acid are not readily obtained from the Diels-Alder reaction, but can be made from the adduct once the maleic anhydride-cyclopentadiene reaction has been done.

Other examples of the flexibility of approach which this invention affords, include the preparation of half esters either directly by radical addition of the perfluoroalkyl iodide to the norbornene dicarboxylic acid half ester, or by reaction of the endo-5-iodo-exo-6-perfluoroalkyl-norbornane-2,3-carboxylic acid with an alcohol; or the preparation of endo-5-iodo-exo-6-perfluoroalkylnorbornane-2,3-dicarboxylic acid imide either from the corresponding amic acid or directly by radical addition of the perfluoroalkyl iodide, in analogy to the two paths shown above for the dicarboxylic acids.

Free radical addition of perfluoroalkyl iodides to dimethyl or diethyl 5-norbornene-endo,endo-2,3-dicarboxylate occurs smoothly at 70° using an azonitrile initiator, and affords chiefly (90-97%) the exo-5-iodo isomer.

By contrast, reaction with 5-norbornene-endo,endo-2,3-dicarboxylic acid anhydride requires a peroxide initiator, and results in a single product, endo-5-iodo-6-perfluoroalkylnorbornane-endo,endo-2,3-dicarboxylic acid anhydride. Surprisingly, addition of perfluoroalkyl iodides to 5-norborene exo,exo-2,3-dicarboxylic acid anhydride also gives the endo-5-iodo product.

The anhydrides are hydrolyzed to the diacids by reaction with aqueous alkali, without significant loss of iodine. The fact that the iodine atom is attached to the hindered endo position probably is significant.

Further variations in procedure which have been found advantageous are choice of solvent, reaction in bulk without added solvent, choice of radical initiator and of reaction time and temperature. Of course, these variables are not all independent of each other. In the large number of examples which are in this specification, these variations are amply demonstrated.

Specific examples which describe alternate processes are Example 6, for the preparation of dimethyl exo-5-iodo-exo-6-perfluorooctylnorbornane-endo,endo-2,3-dicarboxylate, Examples 21 and 25 for the preparation of monomethyl and dimethyl esters of this acid and Example 27 for the preparation of the endo-5-iodo isomer of this acid.

A further modification of this invention is the preparation of iodine-free products. Thermal treatment of dialkyl exo-5-iodo-exo-6-perfluoroalkylnorbornane endo,endo-2,3-dicarboxylates afforded a gamma-lactone in excellent yield. Alkyl iodide is eliminated (e.g., methyl iodide from methyl ester.)

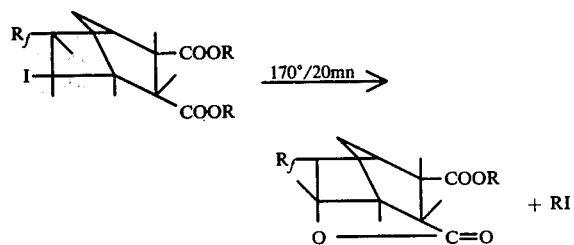

The corresponding endo-5-iodo isomers do not react. When treated with base in an anhydrous medium the same exo-5-endo esters undergo cyclization to a nortricyclene derivative, again in a stereospecific fashion. Certain diamines or alkoxide ion functioned successfully as bases.

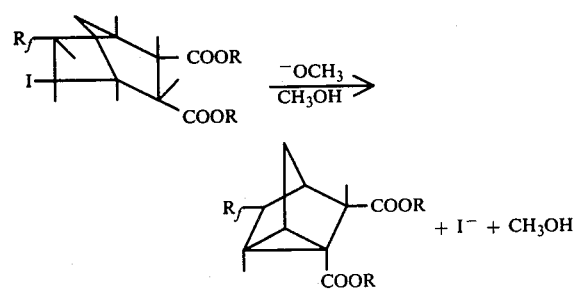

Iodine is also removed chemically by a reaction of the anhydride with zinc and acid.

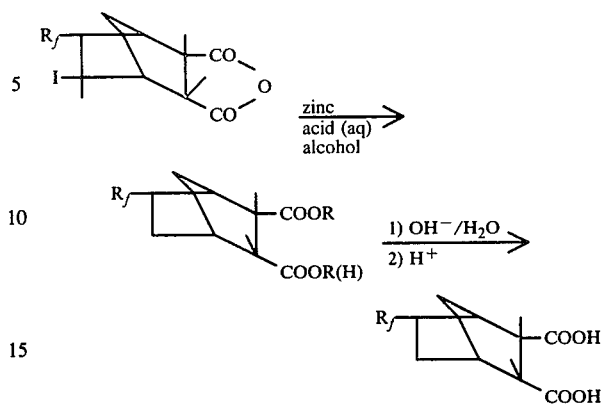

Exo-5-iodo ester with anhydrous HCl in an alcohol solution reacts with zinc to give dialkyl exo-5-perfluoroalkylnorbornance-endo,endo-2,3-dicarboxylate.

The perfluoroalkyl iodides employed in the preparation of the compounds of this invention are well known in the prior art. The iodides may be represented by the formula $R_f I$ where the $R_f$ is as defined above. Illustrative examples of $R_f I$ compounds are as follows:

$(CF_3)_2CFI$ $CF_3(CF_2)_n I$, $n = 2,3,4,5,6,7$ $(CF_3)_2CFO(CF_2CF_2)_m I$, $m = 1,2,3$

EXAMPLE 1

Preparation of Dimethyl exo,endo-5-Iodo-exo-6-isoperfluoropropyl-endo,endo-2,3-Norbornane Dicarboxylate A Fischer-Porter aerosol tube was charged with dimethyl 5-norbornene-endo,endo-2,2-dicarboxylate (8.33g., 0.0396 mole), 2-iodoperfluoropropane (14.80g., 0.0500 mole) and azobisisobutyronitrile (ABN, 0.246g., 1.50 mmole), cooled to $-78°$, evacuated and filled with nitrogen three times and heated at 70.0° in an oil bath for 7.5 hrs. The product was heated to 123° in vacuo (0.40mm) and $(CF_3)_2CFI$ (1.00g, 6.8%) was pumped off and recovered. The residual oil, which would not distill under these conditions, weighed 20.0g (99% conversion). Nuclear magnetic resonance and gas chromatographic analyses showed that the 5-iodo compound in exo and endo configuration comprised 41 and 38% of the mixture. Thus the branched chain $R_f$ group gave a mixture of products.

ANAL. Calcd for $C_{14}H_{14}F_7IO_4$: C, 33.22; H, 2.79; F, 26.28; I, 25.07. Found: C, 35.24; H, 3.19; F, 22.71; I, 26.18.

In Table I are listed additional examples, in which analogous adducts were obtained from dimethyl 5-nonbornene-endo,endo-2,3-dicarboxylate and a series of perfluoroalkyl iodides. In each case only one of the two possible isomeric adducts was obtained in substantial amount; that is, reaction occurred in a stereo-selective way, resulting in 90-97% of the 5-exo-iodo isomer.

Example 6 give additional information, including detailed NMR evidence. Example 7 shows that if the temperature is not controlled, a mixture of isomeric adducts is obtained, as occurred when benzoyl peroxide was used as initiator with the dimethyl ester. Example 8

TABLE I

Preparation of Dimethyl exo-5-iodo-exo-6-perfluoroalkyl-endo,endo-2,3-Norbornane Dicarboxylate

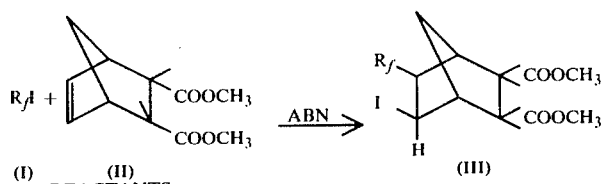

| | (I) REACTANTS | | (II) | ABN | CONDITIONS | | PRODUCT | |
|---|---|---|---|---|---|---|---|---|
| EX. NO. | $R_f$ | wt (mmol) | wt (mmol) | wt (mmol) | TIME hr | TEMP °C | CONV % | M.P. °C |
| 2 | $CF_3(CF_2)_3$ | 17.3g. (50.0) | 8.33 (40.0) | 0.246g. (1.50) | 21.2 | 70 | 93.0 | 95–96.5 (ligroine) |
| 3 | $CF_3(CF_2)_5$ | 53.52g. (120.0) | 22.90g. (108.9) | 0.493g. (3.00) | 17 | 70 | 86.9 | 94.5–95.5 (C Cl$_4$) |
| 4 | $CF_3(CF_2)_7$ | 27.3g. (50.0) | 5.96g. (25.0) | 0.328g. (2.00) | 16 | 70 | 96.0 | 84–86 (C Cl$_4$/ligroine) |
| 5 | $CF_3(CF_2)_n$ (n=5,7,9) | 130g. (225) | 40.0g. (190) | 1.575g. (9.595) | 17 | 70 | 96.0 | |

$$1 = $$ 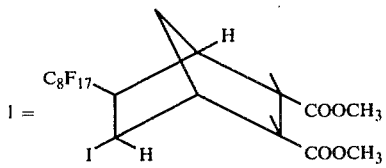

EXAMPLE 6

Preparation of Dimethyl exo-5-Iodo-6-Perfluorooctyl-endo,endo-2,3-Norbornane Dicarboxylate 1-Iodoperfluorooctane (49.14g. 90.0 mmol), dimethyl 5-norbornene-endo,endo-2,3-dicarboxylate (15.78g, 75.0 mmol, 99% by VPC) and ABN (0.492g, 3.00 mmol) were charged to a Fischer/Porter pressure tube, evacuated and filled with nitrogen at −78°. After heating at 70° for 15 min, during which time the tube was occasionally shaken, the two layer mixture became miscible. After 16.5 hr at 70° the cloudy solution was poured and scraped out of the tube, 63.76g, mp 66°–74° (initial sample). A 1.00g sample was recrystallized from carbon tetrachloride/ligroine mixture; it gave 0.9g in three fractions, all mp 84°–86°.

ANAL. Calcd for $C_{19}H_{14}F_{17}IO_4$: C, 30.18; H, 1.87; F, 42.71; I, 16.78. Found: C, 30.31; H, 1.76; F, 42.49; I, 16.39.

EXAMPLE 7

Radical Addition of $C_8F_{17}I$ to Dimethyl 5-Norbornene-2,3-endo,endo-Dicarboxylate Initiated by Benzoyl Peroxide 1-Iodoperfluorooctane (16.4g, 0.0300 mol), dimethyl 5-norbornene-endo,endo-2,3-dicarboxylate (5.25g, 0.0250 mol) and benzoyl peroxide (0.1000g, 0.4219 mmol) was heated in an oil bath under nitrogen. As the temperature reached 85° the reaction temperature shot up to 150°, the colorless solution turned pink in color, and the flask was quickly cooled in a bath of cold water. After one minute the flask was returned to the bath at 108°, and a sample removed for analysis. VPC showed 1% of starting materials. A sample of the isomeric mixture was separated by preparative VPC and the constitution and configuration of the pure substances was determined.

EXAMPLE 8

Radical Addition Initiated by Ultraviolet Light

1-Iodoperfluorooctane (16.4g, 0.0300 mol), dimethyl 5-norbornene endo,endo-2,3-dicarboxylate (5.26g, 0.0250 mol) and 25 ml of ligroine (bp 60°–70°) was charged to a mercury vapor ultraviolet light reactor, fitted with a reflux condenser and a nitrogen gas inlet tube at the bottom. The reactor was allowed to stand at room temperature for 15 hr at 25° to 35°. A dark green colored solid had precipitated in the lower part of the reactor which was dissolved out with hot ligroine. The cold solution and precipitated product was filtered, yielding 8.00g, mp 82°–87° (42%), of a solid. This was essentially pure 1, according to NMR. The filtrate was evaporated off leaving 10.72g of solid. VPC analysis of the solid product showed it to contain 95% of 1.

Free Radical Addition of Perfluoroalkyl Iodides to 5-Norbornene Anhydrides

In contrast to reaction with dimethyl 5-norbornene-2,3-dicarboxylates addition to the anhydrides did not take place using azonitrile initiators. Instead it was found that benzoyl peroxide was an efficient catalyst. Examples 9 through 17 show how various products may be obtained, and disclose the correct structure. Surprisingly, addition occurred in such a way as to place the iodine atom in the indo position. This was true for both the exo-anhydride and for the endo-anhydride. Isomeric products resulting from random orientation were not obtained.

EXAMPLE 9

Preparation of endo-5-Iodo-exo-6-Perfluorohexyl-exo,exo-2,3-Norbornane Dicarboxylic Acid Anhydride A round bottom flask was fitted with a nitrogen inlet, reflux condenser, magnetic stirring bar, and heated by an oil bath. 1-Iodoperfluorohexane (17.84g, 0.0400 mole), 5-norbornene-exo-exo-2,3-dicarboxylic acid anhydride (mp 139°-142°, 4.10g, 0.0250 mole) and benzoyl peroxide (0.200g, 0.826 mmol) were charged to the flask and heated to 110°. A clear solution was formed. After 5.5 hr the product mixture was allowed to cool. The solid was recrystallized from 50 ml of ligroine (bp 60°-70°) and gave adduct in three fractions, mp69°-71°, 14.62g (95.84%). Infrared spectrum gave absorption bands due to C=O at 1770 and 1790 cm$^{-1}$. The following structure was confirmed by an NMR spectrum taken at 100.1 MHz in $CDCl_3$:

EXAMPLES 11 to 16

Preparation of endo-5-Iodo-exo-6-Perfluoroalkyl-endo,endo-2,3-Norbornane Dicarboxylic Acid Anhydrides Following the procedure of Examples 9 and 10, reaction of perfluoroalkyl iodides ($R_fI$) with 5-norbornene-endo,endo-2,3-dicarboxylic acid anhydride gave adducts listed in Table II. The analyses of the adducts are also listed in Table II. Samples for analysis were recrystallized in the indiated solvents. Structures of adducts were ascertained by NMR analysis.

TABLE II

Preparation of endo-5-iodo-exo-6-perfluoroalkyl-endo,endo-2,3-Norbornane Dicarboxylic Anhydrides

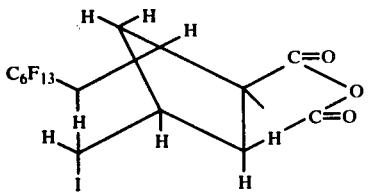

| | REACTANTS | | | CONDITIONS | | PRODUCT | |
|---|---|---|---|---|---|---|---|
| | I | II | | | | | |
| EX. NO. | $R_f$ | wt (mol) | wt (mol) | BPO wt | TIME hr | TEMP °C | CONV % | M.P. °C |
| 11 | $(CF_3)_2CF$ | 29.6g. (.100) | 13.47g. (.080) | .3633g | 5 | 110 | 70 | 141 (ligroine/ethyl acetate) |
| 12* | $CF_3(CF_2)_3$ | 34.6g. (.100) | 13.47g. (.080) | .3633g. | 4 | 110 | 85 | 115-117 (same) |
| 13 | $(CF_3)_2CF\ OCF_2CF_2$ | 41.2g. (.100) | 13.46g. (.080) | .3633g. | 4.5 | 110 | 90 | 158-161 (same) |
| 14 | $CF_3(CF_2)_5$ | 20.7g. (.046) | 4.10g. (.025) | .1500g. | 1.5 | 105 | 100 | 144-146 (benzene) |
| 15 | $CF_3(CF_2)_7$ | 19.1g. (.035) | 4.10g. (.025) | .2000g. | 2 | 105 | 100 | 157-159 (benzene) |
| 16 | $CF_3(CF_2)_7$ | 49.2 (.090) | 12.3g. (.1075) | .4500g. | 3 | 108 | 100 | 157-159 (ethyl acetate/ligroine) |

ANAL. Calcd for $C_{15}H_8F_{13}IO_3$: C, 29.53; H, 1.32; F, 40.48; I, 20.49. Found: C, 29.59; H, 1.11; F, 40.98; I, 20.49.

EXAMPLE 10

Preparation of endo-5-Iodo-exo-6-Perfluorooctyl-exo,exo-2,3-Norbornane Dicarboxylic Acid Anhydride.

Following the procedure of Example 9 1-iodoperfluorooctane (16.4g, 0.0300 mole), 5-norbornene-exo,exo-2,3-dicarboxylic acid anhydride (4.10g, 0.0250 mole) and benzoyl peroxide (0.1000g, 0.413 mmole) when heated for 1.5 hr at 105°-112°, gave an adduct in 100% yield. Unreacted 1-iodoperfluorooctane (3.66g, 100%) was removed by distillation at the water pump. Solid product 17.78g, mp 105°-110°, remained in the flask. A 2.00g portion was recrystallized from benzene, mp 111°-113°. NMR spectrum analysis confirmed the structure of the product.

ANAL. Calcd for $C_{17}H_8F_{17}IO_3$: C, 28.75; H, 1.13; F, 45.48; I, 17.87. Found: C, 28.79; H, 0.82; F, 45.72; I, 17.86.

EXAMPLE 17

Endo-6-Iodo-exo-5-Perfluorooctyl-endo,endo-2,3-Norbornane Dicarboxylic Acid Anhydride 5-Norbornene-endo,endo-2,3-dicarboxylic anhydride (8.21g, 0.0500 mole), 1-iodo-perfluorooctane (56.6g, 0.104 mole) and ABN (0.164g, 1.00 mmole), under nitrogen, was stirred by a magnet bar and heated in oil bath. The mixture was heated to 135° and ditertbutyl peroxide (0.32g, 2.2 mmole) was added. Exothermic reaction occurred and at 140° the solid dissolved. After four hours at 140°-142° another 0.16g portion of ditertbutyl peroxide was added, and kept at 142° for one hour. The solution became dark red in color. Now at the water pump 1-iodoperfluorooctane (bp 70°/35 mm, 28.0g) was removed, leaving 35.0g (99%) of solid adduct mixture. A portion was recrystallized from ligroine to which sufficient ethyl acetate was added to dissolve the solid, mp 157°-159°. Another sample was recrystallized from ligroine-benzene, mp 153°-156°. Fractional crystallization was attempted using ligroine-chloroform but lower melting mixtures were obtained.

ANAL. Calcd for $C_{17}H_8F_{17}IO_3$: C, 28.75; H, 1.13, F, 45.48; I, 17.84. Found: C, 28.65; H, 1.06; F, 45.49; I, 17.75.

EXAMPLE 18

Hydrolysis of endo-5-Iodo-exo-6-Perfluorooctyl-norbornane-endo-endo-2,3-Dicarboxylic Acid Anhydride to the Diacid Anhydride (7.4036g, 0.0100 mole), 75 ml of water and 10.00 ml (0.0600 mole) of 6N sodium hydroxide were heated for 6.0 hr at 63°–70°, while stirring. The clear, alkaline solution was cooled, and the sodium salt precipitated as shiny flakes. The slurry was diluted with 75 ml of ethanol, heated to 55° and acidified with 14.00 ml of 6N HCl, while stirring. The precipitated paste was diluted further with 200 ml of water and collected. After rinsing with water and drying, the solid diacid weighed 7.23g, mp (sinter 147°) 150°–154°(dec.). It was recrystallized from 100 ml of benzene containing enough 95% ethanol to dissolve at the boil; wt. 3.30g, mp 167°–168°(dec). After boiling the filtrate down to 75 ml a fraction, wt 1.18g, mp 165°–166°, and further, wt. 0.39g, mp 152° were obtained. All fractions showed bonded OH and the C=O bands in the infrared.

ANAL. Calcd for $C_{17}H_{10}F_{17}IO_4$: C, 28.04; H, 1.38; F, 44.36; I, 17.43. Found: C, 28.05; H, 1.26; F, 43.84; I, 17.04.

EXAMPLE 19

Hydrolysis of endo-5-Iodo-exo-6-Perfluorooctyl-norbornane-exo,exo-2,3-Dicarboxylic Acid Anhydride to the Diacid Anhydride (1.000g. 1.41 mmole) and 10 ml of water were heated on a steam bath at 90° for a half hour. A thick paste formed; it was cooled to 20° and collected, wt. 1.00g, mp 133°–134°. The sample reverted to the

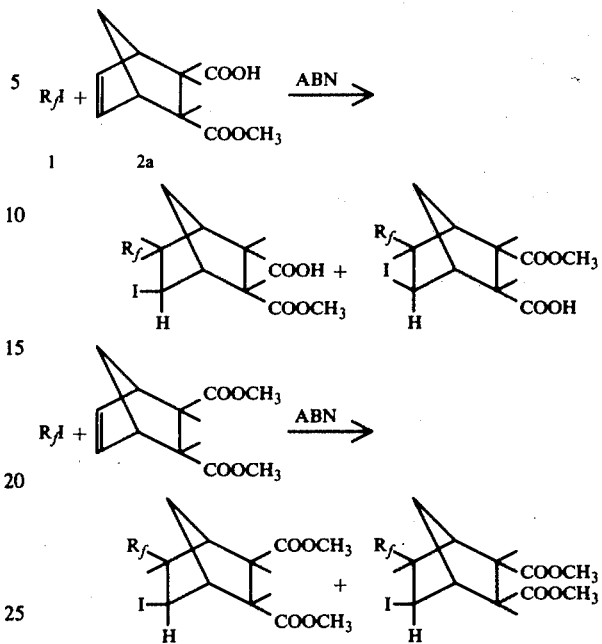

anhydride (mp 113°) upon drying in an oven at 90° for 24 hr.

ANAL. Calcd for $C_{17}H_{10}F_{17}IO_4$: C, 28.04; H, 1.38; F, 44.36; I, 17.43. Found: C, 28.07 H, 1.52; F, 44.4; I, 17.13.

EXAMPLES 20 to 24

Perfluoroalkyl iodides reacted readily with dialkyl 5-norbornene-trans-dicarboxylates or with half alkyl esters such as methy 5-norbornene-endo-2-carboxylate-endo-3-carboxylic acid, using azonitrile initiator. Examples are listed in Table III. In each case isomeric mixtures were formed which resulted in low melting products. By means of NMR analysis and product identity studies it was determined that random reaction occurred, and not stereoselectively.

In Table III the following reactions are summarized:

TABLE III
Preparation of exo-5-iodo-exo-6-perfluoroalkylnorbornane-x-x-2,3-Dicarboxylic Acid Esters

| | REACTANTS | | | CONDITIONS | | PRODUCT | |
|---|---|---|---|---|---|---|---|
| EX. NO. | $R_f$ | 1 wt (mmol) | Norbornene Derivative 2a wt (mmol) | ABN wt (mmol) | TIME hr | TEMP °C | CONV % | REMARKS |
| 20 | $C_6F_{13}$ | 104.5g. (220) | 16.41g. 2a[1] (100.0) | 0.500g. (3.00) | 16 | 70° | 98 | soft solid |
| 21 | $C_8F_{17}$ | 54.6g. (110) | 6.60g. 2a[1] (50.0) | 0.350g. (2.13) | 24 | 72° | 90 | viscous liquid |
| 22 | $C_6F_{13}$ | 13.4g. (30.0) | 5.26g. 2b (25.0) | 0.164g. (1.00) | 21.5 | 70° | 100 | isomeric adducts |
| 23 | $C_8F_{17}$ | 18.35g. (33.6) | 5.26g. 2b (25.0) | 0.164g. (1.00) | 16.5 | 70° | 93 | isomeric adducts |
| 24 | $C_8F_{17}$ | 19.11g. (35.0) | 5.96g. 2c[2] (25.0) | 0.164g. (1.00) | 18.5 | 70° | 94 | isomeric adducts |

[1]Added two-fold excess of methanol to anhydride, formed 2a in situ.
[2]trans-diethyl ester used ELEMENTAL ANALYSES for the adducts of Examples 22, 23 and 24:

| | CALCULATED | | | |
|---|---|---|---|---|
| EX. NO. | C | H | F | I |
| 22 | 31.11 | 2.15 | 37.64 | 19.34 |
| 23 | 30.31 | 1.76 | 42.49 | 16.39 |
| 24 | 32.16 | 2.31 | 41.19 | 16.18 |
| | FOUND | | | |
| 22 | 31.32 | 2.18 | 37.53 | 18.61 |
| 23 | 30.15 | 1.84 | 43.93 | 16.76 |
| 24 | 32.37 | 2.34 | 41.48 | 16.08 |

EXAMPLE 25

Preparation of Dimethyl exo-5-Iodo-exo-6-Perfluorooctylnorbornane-endo,endo-2,3-dicarboxylate via the Half Ester and Acid Chloride The product of Example 21 (7.10g, 10.0 mmole, about 90% pure) and thionyl chloride (1.67g, 14.0 mmole) was heated at 45°–46° for 1 hr. Benzene (1 ml) was added and volatile material removed at the water pump. Methanol (15 ml) was added and kept at 40° for 1 hr, and pumped off again. The residue (7.44g) was recrystallized from ligroine and methanol, to give 3.77g, mp 80°-83° (Sample 1) and three small fractions.

The experiment was repeated using 7.46g (10.5 mmole) of the half ester of Example 21 with thionyl chloride (2.38g, 20.0 mmole). To the residue was added pyridine (0.83g, 10.5 mmole) and methanol (6 ml) and kept at 50° for 2 hr. The esterified product was stirred with water (30 ml), collected and dried, wt 6.68g (90%) (Sample 2). Ir showed a weak band at 1780 cm$^{-1}$ and the ester C=O at 1640 cm$^{-1}$. NMR showed that the product contained 80-90% of dimethyl exo-5-iodo-6-exoperfluorooctyl-endo,endo-2,3-dicarboxylate (see Example 6). Recrystallization from carbon tetrachloride and ligroine gave 4.26g mp 73°-80°; when repeated, 2.77g, mp 78°-82° (Sample 3). VPC analyses was obtained for the three samples. This example shows that addition of perfluorooctyl iodide to the half ester occurred in the same way sterically, as for the dimethyl ester. Also, subsequent reactions of the carboxyl roup did not affect the iodine atom.

EXAMPLE 26

Preparation of Dimethyl exo-5-Iodo-exo-6-Perfluorohexyl-Norbornane-endo,endo-2,3-dicarboxylate via the Half Ester and Acid Chloride The procedure of Example 25 was repeated using the product from Example 20 as the starting material. Reaction with methanol was continued for 3 hr. at 55°-65°, and resulted in a 97.8% yield of product, mp 81°-87°. Recrystallization from ligroine and methanol two times gave pure dimethyl exo-5-iodo-exo-6-perfluorohexyl-endo,endo-2,3-dicarboxylate, mp 94°-96°. An infrared spectrum showed bands at 1750, 1745 and 1705 cm$^{-1}$ (Nujol mull). VPC analysis showed that the origninal sample contained 10% of an unknown substance, and NMR analysis indicated that the recrystallized sample was a pure substance of the structure given.

ANAL. Calcd for $C_{16}H_{11}F_{13}IO_3Cl$: C, 29.09; H, 1.68; F, 37.39. Found: C, 30.33; H, 2.24; F, 35.97.

The results of Examples 20, 21, 25 and 26 show that addition of perfluoroalkyl iodides to the half ester occurs in the same way as to the dialkyl esters.

EXAMPLE 27

Preparation of Dimethyl endo-5-Iodo-exo-6-Perfluorooctylnorbornane-exo-exo-2,3-dicarboxylate from the Anhydride via the Half Ester and Acid Chloride Endo-5-Iodo-exo-6-perfluorooctylnorbornane-exo-2,3-dicarboxylic anhydride (Example 10), 7.10g, 0.0100 mol) and methanol 30 ml, 24g, 0.74 mol) was heated at reflux (65°) for 18 hr, and the excess methanol removed by distillation. The product was a single isomer, mp 172°-174°. An IR spectrum of the solid (half ester) showed $v_{C=O}$ 1735 and 1710 cm$^{-1}$ (ester and acid, resp.). A sample was removed for anaylsis (see Below). Thionyl chloride (29 ml, 37.5g, 0.32 mol) was added and allowed to react for 2.5 hr at 59°-68°. Again the excess reactant was removed, pumping down to 16 mm pressure. An IR spectrum showed $v_{C=O}$ 1790 and 1740 cm$^{-1}$ (COCl and ester) of the acid chloride, methyl ester. Methanol (20 ml, 15.8g, 0.50 mol) was added and the solution heated under reflux (65°) for 16 hr; when excess methanol was removed a viscous oil (7.0g) remained, which became solid (sinter 53°) mp 54°-57° (Fisher-John's block). IR spectrum showed $v_{C=O}$ 1735 cm$^{-1}$ of the dimethyl ester. A sample (2.20g) was recrystallized from pentane, seeded with original solid, chilled to 0°; wt 0.082g, mp unchanged; (2), wt 0.542g, mp (sinter 47°) 48°-55°. IR spectrum differed from endo,endo-2,3- and exo,endo-2,3-diesters in the fingerprint region.

ANAL. Calcd for $C_{18}H_{12}F_{17}IO_4$: C, 29.13; H, 1.63; F, 43.52; I, 17.10. Found (Half Ester): C, 29.02; H, 1.75; F, 42.85; I, 16.45.

ANAL. Calcd for $C_{19}H_{14}F_{17}IO_4$: C, 30.18; H, 1.87; F, 42.71; I, 16.78. Found: C, 30.43; H, 1.87; F, 42.22; I, 16.53.

Examples 28, 29 and 30 describe the preparation and reaction of a gamma-lactone methyl ester, by intramolecular reaction of dimethyl exo-5-iodo-6-exo-perfluorooctylnorbornane-endo,endo-2,3-dicarboxylate. The reaction was stereospecific, as the corresponding endo-5-iodo isomer failed to react. The ester was converted to a pure, crystalline caboxylic acid, by hydrolysis (Example 30).

Examples 31, 32 and 33 also describe the conversion of products of this invention to iodine-free derivatives. In Example 31 iodine is removed by cyclization to a nortricyclene compound, again stereospecifically from the dimethyl exo-5-iodo ester. Chemical reduction of diacid or dialkyl esters by means of zinc and acid also results in dehalogenated products of Examples 32 and 33.

EXAMPLE 28

Preparation of Methyl exo-6-Perfluorooctyl-endo-5-hydroxynorbornane-endo-2-carboxylate-endo-3-carboxylic acid gamma lactone from Dimethyl exo-5-Iodo-exo-6-Perfluorooctylnorbornane-endo,endo-2,3-Dicarboxylate Dimethyl exo-5-iodo-exo-6-perfluorooctylnorbornane-endo,endo-2,3-dicarboxylate (Example 6) was prepared by addition of iodo-perfluorooctane to dimethyl 5-norbornene-endo,endo-2,3-dicarboxylate, using azo-bis-isobutyronitrile initiator at 70°. A quantitative yield of isomeric adducts (93% of exo-5-iodo isomer by VPC analysis) was obtained which gave pure exo-5-iodo isomer in 61% recovery on recrystallization from ligroine and methanol.

In a 250 ml, round bottom flask, fitted with a condenser leading to a Dry Ice cooled trap was placed the exo-5-iodo dimethyl ester (73.8g, 0.0977 mol), and evacuated to 20 mm at the water pump. The flask was heated to 171° in an oil bath and, stirring by a magnet bar, gave smooth evolution of methyl iodide during two hours at 170°-174°. The cold trap liquid weighed 9.8g (71% as iodomethane). The residue (61.52g, 100%) was dissolved in hot benzene (400 ml), treated with decolorizing carbon, and gave shiny, white crystals of gamma lactone; 45.54g, 5.37g and 1.82g in three fractions (87.8%), mp 127°-127.5°, and 125°-127°. A residue of 8.60g was recovered from the final filtrate.

ANAL. Calcd for $C_{18}H_{11}F_{17}O_4$: C, 35.19; H, 1.80; F, 52.58. Found: C, 35.07; H, 1.84; F, 52.34.

EXAMPLE 29

Conversion of Methyl exo-6-Perfluorooctyl-endo-5-Hydroxynorbornane-endo-2-carboxylate-endo-3-Carboxylic Acid gamma Lactone by Hydrolysis to exo-6-Perfluorooctyl-endo-5-hydroxynorbornane-endo-2-carboxylic acid endo-3-carboxylic acid gamma lactone To a solution of NaOH (1.2g, 0.030 mol) in 2 ml of water and 18 ml of methanol was added the lactone methyl ester (5.34g, 0.00869 mol) and the suspension heated at 60°–85° for three hours, stirring by magnet bar. Acetic acid (15 ml) was added and the clear solution poured into 25 ml of water while stirring. The sodium salt precipitated, wt 4.36g (83.6%). It was suspended in 95% ethanol (70 ml), 3–4 ml of 2N HCl added and the clear solution at the boil deposited a little salt; when cooled it gave crystals of lactone acid, 1.89g, mp 174°–175°. Concentration of the filtrate to 35 ml gave additional crops; a total recovery of 79%. The first fraction of (0.6001g) was recrystallized again from 80% ethanol, wt 0.5734g, mp 174°–176° (resolidifies at 167°).

ANAL. Calcd for $C_{17}H_9F_{17}O_4$: C, 34.01; H, 1.55; F, 53.81. Found: C, 34.08; H, 1.55; F, 53.89.

EXAMPLE 30

Preparation of Dimethyl exo-7-Perfluorooctylnortricyclene-endo-3-Carboxylate-2-Carboxylate from Dimethyl exo-5-Iodo-exo-6-perfluorooctylnorbornane-endo,endo-2,3-Dicarboxylate Sodium methoxide (1.22g, 0.0210 mole) was added to a slurry of dimethyl ester (Example 6, 90% pure, 15.13g, 0.0200 mole) while stirring by magnet bar and heated to 40° in an oil bath. At first the solution cleared and then a thick precipitate began to form in five minutes. After 5 hr at 36°–40° the thick paste was allowed to stand overnight. Dilute hydrochloric acid (30 ml, 1N) was added and the product extracted with chloroform (3 times, 15 ml), and once with dilute aqueous bisulfite and dried (MgSO₄). Evaporation of solvent gave 13.56g (97%) of solid product which NMR analysis indicated to be 90% pure substance. Recrystallization from ligroine gave product, mp 83.5°–84.5°.

The nortricyclene derivative was obtained in 50% yield by reaction of the dimethyl ester with N,N,N'-trimethyl-1,3-propanediamine. Reaction of the dimethyl ester with N,N-dimethylpropanediamine in benzene solution at 70° for four hours gave the nortricyclene derivative in 59% yield.

EXAMPLE 31

Reduction of endo-5-iodo-exo-6-perfluorooctylnorbornane-endo,endo-2,3-dicarboxylic anhydride to exo-6-perfluorooctylnorbornane-endo,endo-2,3-dicarboxylic Acid Zinc (Baker's, 30 mesh, 3.00g, 0.0460 mol), water (75 ml), hydrochloric acid (concd, 12 M), ethanol (20 ml) and the title compound (16.7g, 0.0235 mol) were stirred by a magnet bar and heated near the boiling point for two hours; during this time two further additions of zinc (3.00g) were made. Then 12M hydrochloric acid (6ml) and ethanol (100 ml) were added to give a clear colorless solution, kept near boiling for 1 hour. It was decanted from a little remaining zinc, into water (200 ml) and extracted with ether (3 times, 25 ml), dried over MgSO₄, and evaporated off to a gummy solid, 17.3g (100%). The impure product (ester) was hydrolyzed in ethanol (75 ml) containing NaOH (2.00g, 0.050 mol) and water (10 ml), by heating for 4 hours at 58°–63°. The mixture was acidified with hydrochloric acid (6N, 10.0 ml), and poured into water (300 ml). The precipitated solid acid was dried, 13.62g (90%) mp 152°–161°; a small portion recrystallized from benzene-alcohol solution, gave pure exo-6-perfluorooctylnorbornane-2,3-dicarboxylic acid, 1.00g, mp 166°–167.5° (gas, decomp). Lower melting, impure product (1.87g) was obtained from the filtrate.

ANAL. Calcd for $C_{17}H_{11}F_{17}O_4$: C, 33.90; H, 1.84; F, 53.63. Found: C, 33.80; H, 1.86; F, 54.09.

EXAMPLE 32

Zinc reduction of Diethyl exo-5-Iodo-exo-6-Perfluorooctylnorbornane-endo,endo-2,3-Dicarboxylate to Diethyl exo-6-Perfluorooctylnorbornane-endo,endo-2,3-Dicarboxylate Diethyl exo-5-iodo-exo-6-perfluorooctylnorbornane-endo,endo-2,3-dicarboxylate was prepared as in Example 2 from diethyl 5-norbornene-endo,endo-2,3-dicarboxylate in 96.0% yield, mp 52°–54°. Diethyl ester (14.0g, 0.0178 mole) was dissolved in 100 ml of ethanol, and while stirring at 60°–75°, saturated with gaseous anhydrous hydrogen chloride. Portions of zinc (10.g, 0.135 mole) were added. The yellow color disappeared and the solution foamed, during 2 hr reaction. Ethanol was distilled off, the liquid decanted into 100 ml of water and extracted 3 times with benzene. The organic extract was dried over MgSO₄ and distilled, heating with an oil bath and without a column. Diethyl exo-6-perfluorooctylnorbornane-endo,endo-2,3-dicarboxylate, bp 138°–145°/0.65 mm, 5.7g (48.6% conv.), and a solid residue (4.0g, 34.1%) were recovered.

ANAL. Calcd for $C_{21}H_{19}F_{17}O_4$: C, 38.31; H, 2.91; F, 49.06. Found: C, 38.70; H, 2.95; F, 48.33.

What is claimed is:

1. A compound having the formula

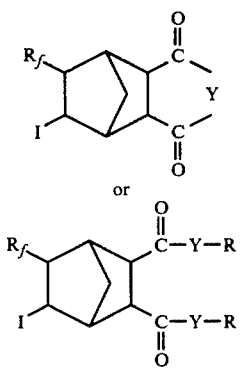

and an isomeric mixture thereof, wherein

Y is independently oxygen or the group $>$ NR

R is independently hydrogen or alkyl of 1 to 24 carbons or each group - YR is independently a halogen, and $R_f$ is a straight or branched chain perfluoroalkyl of 1 to 18 carbon atoms or said perfluoroalkyl substituted by a perfluoroalkoxy group of 2 to 6 carbon atoms.

2. A compound according to claim 1 of the formula

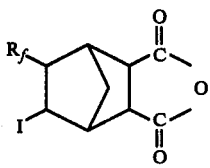

wherein $R_f$ is straight or branched chain perfluoroalkyl of 1 to 18 carbon atoms or said perfluoroalkyl substituted by a perfluoroalkoxy group of 2 to 6 carbon atoms.

3. A compound of claim 1 of formula II wherein R is alkyl and an isomeric mixture thereof.

4. A compound of claim 1 of formula II where Y is > NR and an isomeric mixture thereof.

5. A compound of claim 1 wherein $R_f$ is a perfluoroalkyl group of 6 to 12 carbon atoms or a mixture of such groups.

6. A compound of claim 4 wherein $R_f$ is a perfluoroalkyl group of 6 to 12 carbon atoms or a mixture of such groups.

7. A compound of claim 1, dialkyl exo, endo-5-iodo-exo-6-perfluoroalkyl-endo,endo-2,3-norbornane dicarboxylate.

8. A compound of claim 1, dialkyl exo-5-iodo-6-perfluoroalkyl-endo,endo-2,3-norbornane dicarboxylate.

9. A compound of claim 2, endo-5-iodo-exo-6-perfluoroalkyl-exo,exo-2,3-norbornane dicarboxylic acid anhydride.

10. A compound of claim 2, endo-5-iodo-exo-6-perfluoroalkyl-endo,endo-2,3-norbornane dicarboxylic acid anhydride.

11. A compound of claim 2, endo-6-iodo-exo-5-perfluoroalkyl-endo,endo-2,3-norbornane dicarboxylic acid anhydride.

12. A compound of claim 1, exo-5-iodo-exo-6-perfluoroalkylnorbornane-2,3-dicarboxylic acid esters.

13. A compound of claim 1, dialkyl endo-5-iodo-exo-6-perfluoroalkyl-norbornane-exo,exo-2,3-dicarboxylate.

* * * * *